US 6,686,465 B2

(12) United States Patent
Ohlbach et al.

(10) Patent No.: US 6,686,465 B2
(45) Date of Patent: Feb. 3, 2004

(54) PREPARATION OF CYCLIC LACTAMS

(75) Inventors: Frank Ohlbach, Dossenheim (DE); Andreas Ansmann, Wiesloch (DE); Peter Bassler, Viernheim (DE); Rolf-Hartmuth Fischer, Heidelberg (DE); Hermann Luyken, Ludwigshafen (DE); Stefan Maixner, Schwetzingen (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/258,943

(22) PCT Filed: Apr. 30, 2001

(86) PCT No.: PCT/EP01/04841
§ 371 (c)(1),
(2), (4) Date: Oct. 29, 2002

(87) PCT Pub. No.: WO01/83444
PCT Pub. Date: Nov. 8, 2001

(65) Prior Publication Data
US 2003/0125544 A1 Jul. 3, 2003

(30) Foreign Application Priority Data
May 3, 2000 (DE) .......................... 100 21 193

(51) Int. Cl.$^7$ ............................ C07D 201/08
(52) U.S. Cl. ....................................... 540/539
(58) Field of Search ........................ 540/539

(56) References Cited

U.S. PATENT DOCUMENTS

| 5,493,021 A | 2/1996 | Barratt et al. | 540/539 |
| 5,495,016 A | 2/1996 | Achhammer et al. | 540/539 |
| 5,512,697 A | 4/1996 | Schnurr et al. | 558/459 |
| 5,527,946 A | 6/1996 | Flick et al. | 558/459 |
| 5,693,793 A | 12/1997 | Ritz et al. | 540/539 |
| 6,100,396 A | 8/2000 | Gayet et al. | 540/539 |

FOREIGN PATENT DOCUMENTS

| WO | 96/22974 | 8/1996 |
| WO | 98/37063 | 8/1998 |
| WO | 99/22974 | 3/1999 |
| WO | 99/28296 | 6/1999 |
| WO | 99/47500 | 9/1999 |

OTHER PUBLICATIONS

Enc.Chem.Tech. 3rd Ed., 1979, 870–881.

Primary Examiner—Bruck Kifle
(74) Attorney, Agent, or Firm—Keil & Weinkauf

(57) ABSTRACT

A process is provided for the preparation of cyclic lactams of formula (II):

$$\left(\begin{array}{c}R1\\R2\end{array}\right)C \underset{n}{\underbrace{\phantom{XXX}}} \begin{array}{c}(CH_2)_m\\ \diagdown \\ C=O \\ / \\ N \\ | \\ H\end{array} \quad \text{(II)}$$

in which n and m can each have the values 0, 1, 2, 3, 4, 5, 6, 7, 8 and 9 and the sum of n+m is at least 3, preferably at least 4, and $R^1$ and $R^2$ are $C_1$–$C_6$-alkyl, $C_5$–$C_7$-cycloalkyl or $C_6$–$C_{12}$-aryl groups,
by reacting a compound (I) of the formula $$H_2N - \left[\begin{array}{c}R^1\\|\\C\\|\\R^2\end{array}\right]_n - [CH_2]_m - R \quad \text{(I)}$$

in which $R^1$, $R^2$, m and n are as defined above and R are [sic] nitrile, carboxamide and carboxylic acid groups, with steam in the gas phase.

27 Claims, No Drawings

PREPARATION OF CYCLIC LACTAMS

The present invention relates to a process for the preparation of cyclic lactams of formula (II):

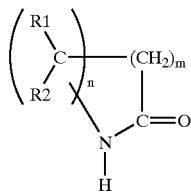

(II)

in which n and m can each have the values 0, 1, 2, 3, 4, 5, 6, 7, 8 and 9 and the sum of n+m is at least 3, preferably at least 4, and $R^1$ and $R^2$ are $C_1$–$C_6$-alkyl, $C_5$–$C_7$-cycloalkyl or $C_6$–$C_{12}$-aryl groups, by reacting a compound (I) of the formula

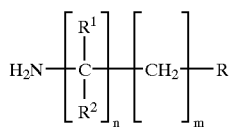

(I)

in which $R^1$, $R^2$, m and n are as defined above and R are [sic] nitrile, carboxamide and carboxylic acid groups, with steam in the gas phase, wherein a) the compound (I) is reacted with steam in the gas phase with the addition, before or after the reaction, of an organic diluent (III) which exhibits a miscibility gap with water under specific quantity, pressure and temperature conditions, to give a mixture (IV) containing a lactam (II), b) the mixture (IV) is converted, before or after the separation of ammonia, under quantity, pressure and temperature conditions such that the diluent (III) and water are liquid and exhibit a miscibility gap, to give a two-phase system consisting of a phase (V) containing a higher proportion of diluent (III) than water, and a phase (VI) containing a higher proportion of water than diluent (III), c) the phase (V) is separated from the phase (VI), and d) the diluent (III) and optionally by-products selected from the group consisting of low-boiling component [sic], high-boiling component [sic] and unreacted compound (I) are separated from the phase (V) to give a lactam (II).

Processes for the preparation of cyclic lactams by reacting omega-aminocarboxylic acid derivatives with steam in the gas phase in the presence of heterogeneous catalysts, for example the preparation of caprolactam from 6-aminocarboxylic [sic] acid nitrile, are generally known.

Thus WO 96/22974, EP-A-659741, WO 99/47500 and WO 99/28296 disclose the reaction of 6-aminocapronitrile with steam in the gas phase in the presence of heterogeneous catalysts to give caprolactam and ammonia, examples of the heterogeneous catalysts used being aluminum oxide, lanthanum phosphates and zirconium dioxide. WO 96/22974 points out that it is not excluded to carry out the cyclization using a diluent which is inert under the reaction conditions, for example an alkane, a cycloalkane, an aromatic hydrocarbon or a halogenohydrocarbon, and thus to have a liquid phase in the reaction mixture.

WO 98/05636 describes the work-up of reaction discharges such as those obtained in the gas phase cyclization of 6-aminocapronitrile with steam in the presence of solid catalysts. To effect said work-up:

a) the bulk of the ammonia formed in the cyclization is separated from the water-containing crude caprolactam, and b) this crude caprolactam is either subjected to a liquid/liquid extraction with the addition of a solvent containing acidic groups, and/or treated with a cation exchanger.

Measure b) extracts all the amines or binds them to the cation exchanger. The principal disadvantage of this work-up is that aminocapronitrile which has not reacted in the cyclization is taken up by the ion exchangers and, when the ion exchanger is regenerated, is obtained as the ammonium salt mixed with ammonium salts of amine by-products, so it cannot be returned to the cyclization. Ammonium salts are also formed in the extraction of the aminocapronitrile with extractants containing acidic groups, and create the same problems.

It is therefore an object of the present invention to provide a process which makes it possible to prepare cyclic lactams (II) from compounds (I) in a technically simple and economic manner, produces high yields of lactam with high conversions of the compound (I) and also minimizes losses of yield in the work-up.

We have found that this object is achieved by the process defined at the outset.

Suitable compounds (I) are aminocarboxylic acids and derivatives thereof, preferably those of general formula I:

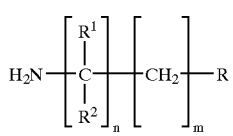

(I)

in which R is carboxylic acid, nitrile and/or carboxamide groups and n and m can each have the values 0, 1, 2, 3, 4, 5, 6, 7, 8 and 9 and the sum of n+m is at least 3, preferably at least 4.

In principle, $R^1$ and $R^2$ can be any kind of substituents, the only proviso being that the desired cyclization reaction is not affected by the substituents. Preferably, $R^1$ and $R^2$ independently of one another are $C_1$–$C_6$-alkyl or $C_5$–$C_7$-cycloalkyl groups or $C_6$–$C_{12}$-aryl groups.

Particularly preferred starting compounds are aminocarboxylic acid nitrites, preferably those of the general formula

in which m has a value of 3, 4, 5 or 6, especially 5. When m=5, the starting compound is 6-aminocapronitrile.

The compound (I) used can be a single compound (I) or a mixture of different compounds (I). The compound (I) used is preferably a single compound.

Omega-aminocarboxylic acid nitrites are obtainable for example by the partial hydrogenation of alpha,omega-dinitriles in the gas or liquid phase, e.g. according to WO 96/20166, WO 96/20916 or WO 96/20165.

Omega-aminocarboxylic acids are obtainable for example by the aminating hydrogenation of omega-formylcarboxylic acids or by the hydrolysis of omega-aminocarboxylic acid esters or omega-aminocarboxylic acid nitriles.

Omega-aminocarboxamides are obtainable for example by the reaction of omega-aminocarboxylic acids and esters thereof with ammonia or by the reaction of omega-aminocarboxylic acid nitrites with water.

The process according to the invention yields the cyclic lactams of formula (II) corresponding to the compound (I):

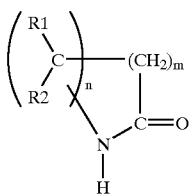

(II)

in which n, m, $R^1$ and $R^2$ are as defined above. Particularly preferred lactams are those in which n=0 and m has a value of 3, 4, 5 or 6. When m=5, the product obtained is caprolactam.

In step a) of the process according to the invention, the above-described compound (I) is reacted with steam in the gas phase, advantageously in the presence of a heterogeneous catalyst and optionally in the presence of an organic diluent (III), to give a mixture (IV) containing a lactam (II).

Suitable heterogeneous catalysts are any of the catalysts described for the gas phase cyclization of a compound (I) to a lactam (II), such as amorphous titanium dioxide in the form of anatase or rutile, aluminum oxide, lanthanum phosphates, hafnium oxide, zirconium dioxide or mixtures thereof, preferably titanium dioxide, aluminum oxide, lanthanum phosphates, zirconium dioxide or mixtures thereof.

The diluent (III) can be added before the cyclization. In this case the diluent (III) is present during the cyclization of the compound (I) in the gaseous reaction mixture, preferably in amounts of 0.1 to 20 g of diluent (III) per gram of compound (I).

It is preferred to add the diluent (III) to the cyclization discharge, for example by quenching the cyclization discharge.

A further possibility is to add the diluent (III) after the separation of ammonia from the mixture (IV).

The diluents (III) used can be organic compounds which exhibit a miscibility gap with water under specific quantity, pressure and temperature conditions, especially below the reaction temperature in the cyclization.

Suitable diluents (III) are $C_4$- to $C_9$-alkanols such as n-butanol, i-butanol or n-pentanol, preferably aliphatic hydrocarbons such as n-hexane, cycloaliphatic hydrocarbons such as cyclopentane or cyclohexane, and especially aromatic hydrocarbons such as benzene, toluene, o-xylene, m-xylene, p-xylene, ethylbenzene, i-propylbenzene or di-i-propylbenzene, and mixtures of such compounds, for example petroleum ethers. The hydrocarbons can carry functional groups such as halogens, for example chlorine, as in chlorobenzene.

Ammonia can also be present in the reaction of step a).

The reaction can advantageously be carried out in the gas phase at temperatures generally of 200 to 450° C., preferably of 250 to 400° C. The pressure should generally range from 0.01 to 20 bar, preferably from 0.1 to 5 bar. The reaction mixture should be predominantly gaseous in this reaction. The residence times generally range from 0.1 to 100 seconds, preferably from 1 to 50 seconds.

The amount of water used in the cyclization should generally be at least 0.5 mol, preferably at least 1 to 50 mol, per mol of compound (I).

The reaction can be carried out in the presence of an inert gas such as nitrogen or a noble gas or mixtures of such gases.

The reaction of step a) gives a mixture (IV) containing a lactam (II).

Provided the mixture (IV) contains ammonia, the ammonia can be separated from the mixture (IV) in step b) after or, preferably, before the phase separation, preferably by distillation, to give an ammonia-free or ammonia-poor mixture (IX). The ammonia can also be separated from the phase (V) and/or the phase (VI) after the phase separation, preferably by distillation.

The mixture (IV) can contain ammonia e.g. if ammonia is formed in the reaction of step a) and/or if ammonia has been added to the reaction mixture in the reaction of step a). Ammonia can be formed in the reaction of step a) e.g. if R is a nitrile or carboxamide group.

The separation can advantageously be effected by distillation, especially at bottom temperatures of 60 to 220° C. and pressures of 1 to 30 bar.

If the mixture (IV) does not contain ammonia—this also being understood as including such small traces of ammonia as would not adversely affect the following process steps—the mixture (IV) and the mixture (IX) are identical.

In step b), according to the invention, the mixture (IX) is converted under quantity, pressure and temperature conditions such that the diluent (III) and water are in liquid form and exhibit a miscibility gap, to give a two-phase system consisting of a phase (V) and a phase (VI).

Preferred quantity, pressure and temperature conditions are such that the constituents of the mixture (VII) are in completely liquid form in the phases (V) and (VI), i.e. no solids precipitate out.

If step a) has been carried out in a homogeneous liquid phase, it is generally possible to separate the mixture (VII) into the two phases (V) and (VI) by choosing an appropriate temperature. A further possibility is to choose appropriate proportions, such as the addition of diluent (III), preferably water.

According to the invention, the phase (V) and the phase (VI) are then separated in step c).

The phase separation can be effected in a manner known per se in apparatuses described for such purposes, for example those known from Ullmann's Encyclopedia of Industrial Chemistry, vol. B3, 5th ed., VCH Verlagsgesellschaft, Weinheim, 1988, pages 6–14 to 6–22.

The optimum apparatuses and process conditions for the phase separation can easily be determined by a few simple preliminary experiments.

In step d), according to the invention, the diluent (III), optionally ammonia and optionally by-products selected from the group consisting of low-boiling component [sic] (VIII), high-boiling component [sic] (VII) and unreacted compound (I) are separated from the phase (V) to give a lactam (II).

In terms of the present invention, low-boiling component [sic] (VIII) are understood as meaning compounds boiling below the lactam (II) and high-boiling component [sic] (VII) are understood as meaning compounds boiling above the lactam (II).

This work-up can advantageously be effected by fractional distillation in one or more, such as 2 or 3, distillation apparatuses.

Suitable apparatuses are those conventionally used for distillation, for example the ones described in Kirk-Othmer, Encyclopedia of Chemical Technology, 3rd ed., vol. 7, John Wiley & Sons, New York, 1979, pages 870–881, such as sieve-plate columns, bubble-cap columns or packed columns.

Preferably, any ammonia and diluent (III) still present are appropriately separated from the phase (V) first. The high-boiling components (VII), the low-boiling components (VIII) and any unreacted compound (I) can then be separated from the lactam (II), individually or together.

Advantageously, all or part of the diluent (III) obtained in step d) can be recycled into step a).

Advantageously, all or part of any high-boiling components (VIII) [sic] and/or low-boiling components (VII) [sic] obtained in step d) can be recycled into step a).

Advantageously, all or part of any unreacted compound (I) obtained in step d) can be recycled into step a).

The phase (VI) obtained in step c) can advantageously be recycled into step a).

Preferably, all or part of the lactam (II) can be separated from the phase (VI) to give a mixture (X), and the low-boiling components (VIII) and/or high-boiling components (VII) can optionally be separated from the resulting lactam (II).

This work-up of the lactam (II) can advantageously be effected by fractional distillation in one or more, such as 2 or 3, distillation apparatuses.

Suitable apparatuses are those conventionally used for distillation, for example the ones described in Kirk-Othmer, Encyclopedia of Chemical Technology, 3rd ed., vol. 7, John Wiley & Sons, New York, 1979, pages 870–881, such as sieve-plate columns, bubble-cap columns or packed columns.

The high-boiling components (VII) and/or low-boiling components (VIII) can be separated from the lactam (II) individually or together.

Advantageously, all or part of the high-boiling components (VII) and/or low-boiling components (VIII) can be recycled into step a).

Particularly preferably, the high-boiling components (VII) are appropriately recleaved before being recycled into step a), as described e.g. in EP-A-793650, EP-A-793651, EP-A-794643 or EP-A-912508. Before the work-up, the lactam (II) obtained from the phase (VI) can also be combined with the crude lactam (II) obtained in step d) and the two worked up together.

The phase (X) can advantageously be recycled into step a).

All or part of the lactam (II) can be separated from the phase (VI) by extraction with a liquid extractant (XI) to give a mixture (XII) containing an extractant (XI) and a lactam (II).

Suitable extractants (XI) are $C_4$- to $C_9$-alkanols such as n-butanol, i-butanol or n-pentanol, preferably aliphatic hydrocarbons such as n-hexane, cycloaliphatic hydrocarbons such as cyclopentane or cyclohexane, and especially aromatic hydrocarbons such as benzene, toluene, o-xylene, m-xylene, p-xylene, ethylbenzene, i-propylbenzene or di-i-propylbenzene, and mixtures of such compounds, for example petroleum ethers. The hydrocarbons can carry functional groups such as halogens, for example chlorine, as in chlorobenzene.

In particular, the extractants (XI) and the diluents (III) have the same or a similar composition.

Thus diluent (III) separated off in step d) can advantageously be used as the extractant (XI).

The aqueous phase (X) remaining from the extraction can advantageously be recycled into step a).

The extractant (XI) and optionally the low-boiling components (VIII), the high-boiling components (VII) and/or unreacted compound (I) can advantageously be separated from the mixture (XII) to give a lactam (II).

This work-up can advantageously be effected by fractional distillation in one or more, such as 2 or 3, distillation apparatuses.

Suitable apparatuses are those conventionally used for distillation, for example the ones described in Kirk-Othmer, Encyclopedia of Chemical Technology, 3rd ed., vol. 7, John Wiley & Sons, New York, 1979, pages 870–881, such as sieve-plate columns, bubble-cap columns or packed columns.

Preferably, the extractant (XI) is appropriately separated from the mixture (XII) first. The high-boiling components, the low-boiling components and any unreacted compound (I) can then be separated from the lactam (II) individually or together.

Advantageously, all or part of the extractant (XI) obtained in the work-up can be recycled into step a).

Advantageously, all or part of any high-boiling components (VII) and/or low-boiling components (VIII) obtained in the work-up can be recycled into step a).

Advantageously, all or part of any unreacted compound (I) obtained in the work-up can be recycled into step a).

The mixture (XII) and the phase (V) can advantageously be used together in step d) of the process according to the invention, it being possible for them to be combined before or during step d). The lactams obtained in the process according to the invention can be used in a manner known per se for the preparation of industrially important polymers such as polyamides.

We claim:

1. In the process for the preparation of cyclic lactams of formula (II)

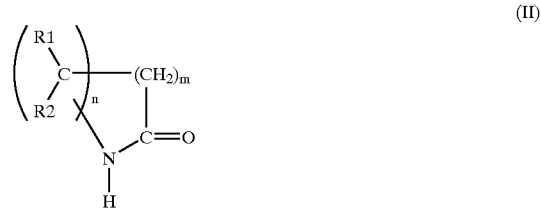

(II)

in which n and m can individually have a value of 0, 1, 2, 3, 4, 5, 6, 7, 8, or 9, the sum of n and m is at least 3 and $R^1$ and $R^2$ denote $C_1$–$C_6$ alkyl, $C_5$–$C_7$ cycloalkyl or $C_6$–$C_{12}$ aryl groups by reaction of a compound (I) of the formula

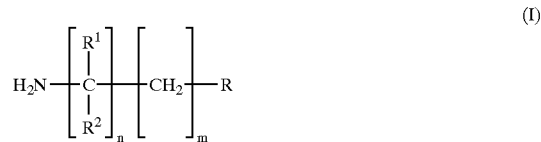

(I)

in which $R^1$, $R^2$, m and n have the meanings stated above and R denotes nitrile, carboxamido and carboxy groups, with steam in the vapor phase, the improvement wherein
a) compound (I) is caused to react with steam in the vapor phase, an organic diluent (III) which is an aliphatic, cycloaliphatic or aromatic hydrocarbon, being added after the reaction, which diluent exhibits a miscibility gap with water under certain conditions of concentration, pressure and temperature, to give a mixture (IV) containing lactam (II)
b) mixture (IV) is subjected, before or after separation of ammonia, to conditions of concentration, pressure and temperature under which diluent (III) and water are present in the liquid state and exhibit a miscibility gap, to give a two-phase system comprising a phase (V) in which the content of diluent (III) is higher than that of water and a phase (VI) in which the content of water is higher than that of diluent (III), c) phase (V) is separated from phase (VI), and
d) from phase (V) diluent (III) and optionally by-products comprising low boilers (VIII), high boilers (VII) and/or uncoverted compound (I) are separated, to give lactam (II).

2. A process as defined in claim 1, wherein the compound (I) used is an aminocarboxynitrile.

3. A process as defined in claim 1, wherein the compound (I) used is an aminocarboxynitrile of the formula

in which m is 3, 4, 5, or 6.

4. A process as defined in claim 1, wherein the compound (I) used is 6-aminocarboxynitrile.

5. A process as defined in claim 1, wherein step a) is carried out in the presence of a heterogeneous catalyst.

6. A process as defined in claim 5, wherein the heterogeneous catalyst used comprises titanium (IV) oxide, aluminum oxide, lanthanum phosphates or zirconium dioxide.

7. A process as defined in claim 1, wherein the reaction is step a) is carried out at a temperature ranging from 200 to 450° C.

8. A process as defined in claim 1, wherein the sum of the concentration of compound (I) and compound (II), based on mixture (IV), is less than 20 wt %.

9. A process as defined in claim 1, wherein the diluent (III) used is ethylbenzene, benzene, toluene, o-xylene, m-xylene or p-xylene.

10. A process as defined in claim 1, wherein separation of ammonia from mixture (IV) is carried out prior to separation of phase (V) specific for step c).

11. A process as defined in claim 1, wherein the reaction in step
a) is carried out in a homogeneous liquid phase.

12. A process as defined in claim 1, wherein the phase (VI) separated in step c) is completely or partially recycled to step a).

13. A process as defined in claim 1, wherein the phase (VI), separated in step c) to give a phase (X) containing less lactam (II) than phase (VI), lactam (II) is partially or completely separated and from the resulting lactam (II) there are separated, optionally, any by-products comprising low boilers (VIII) and high boilers (VII).

14. A process as defined in claim 1, wherein from phase (VI) lactam (II) is partially or completely separated by extraction with an extracting agent (XI) to give a mixture (XII), containing extracting agent (XI) and lactam (II), and a phase (X), containing less lactam (II) than phase (VI).

15. A process as defined in claim 13, wherein phase (X) is completely or partially recycled to step a).

16. A process as defined in claim 14, wherein the extracting agent (XI) and any by-products comprising low boilers (VIII) and high boilers (VII) are separated from mixture (XII) to give lactam (II).

17. A process as defined in claim 14, wherein mixture (XII) and phase (V) are used concurrently in step d).

18. A process as defined in claim 14, wherein extracting agent (XI) and diluent (III) are one and the same or have the same composition.

19. A process as defined in claim 12, wherein lactam (II) is separated only from that partial stream of phase (VI) which is not recycled to the cyclization stage and the remaining portion of phase (VI) is completely or partially recycled to step a) without recovery of lactam (II).

20. A process as defined in claim 1, wherein unconverted compound (I) separated in step d) is partially or completely recycled to step a).

21. A process as defined in claim 1, wherein high boilers (VII) separated in step d) are completely or partially recycled to step a).

22. A process as defined in claim 21, wherein the high boilers (VII) separated in step d) contain at least 20 wt % of lactam (II).

23. A process as defined in claim 1, wherein diluent (III) separated in step d) is partially or completely recycled to step a).

24. A process as defined in claim 1, wherein low boilers (VIII) separated in step d) are partially or completely recycled to step a).

25. A process as defined in claim 14, wherein the extracting agent (XI) used is diluent (III) separated in step d).

26. A process as defined in claim 14, wherein lactam (II) is completely or partially extracted with water from phase (V) or phase (XII) to give a phase (XIII), containing a lesser amount of lactam (II), and a phase (XIV), containing a greater amount of lactam (II), and phase (XIII) is completely or partially recycled to step a).

27. A process as defined in claim 21, wherein the stream of high boilers (VII) recycled to step a) is combined with a recycled stream (VI) or (X) before reaching step a).

* * * * *

UNITED STATES PATENT AND TRADEMARK OFFICE
CERTIFICATE OF CORRECTION

PATENT NO. : 6,686,465 B2
DATED : February 3, 2004
INVENTOR(S) : Ohlbach et al.

It is certified that error appears in the above-identified patent and that said Letters Patent is hereby corrected as shown below:

Column 7,
Line 4, "uncoverted" should be -- unconverted --;
Line 21, "is" should be -- in --;
Line 24, "concentration" should be -- concentrations --.

Signed and Sealed this

Sixth Day of July, 2004

JON W. DUDAS
*Acting Director of the United States Patent and Trademark Office*